United States Patent [19]

Jaselskis et al.

[11] Patent Number: 5,209,129
[45] Date of Patent: May 11, 1993

[54] SUBSURFACE SAMPLER

[75] Inventors: Edward J. Jaselskis, Ames, Iowa; George F. Czapar, Rochester, Ill.

[73] Assignee: Iowa State University Research Foundation, Inc., Ames, Iowa

[21] Appl. No.: 726,311

[22] Filed: Jul. 5, 1991

[51] Int. Cl.$^5$ .............................................. G01N 1/04
[52] U.S. Cl. ............................... 73/864.64; 73/864.74; 175/20
[58] Field of Search ........... 73/864.64, 864.63, 864.74, 73/864.86, 863.82, 866.5; 175/20, 58; 166/100

[56] References Cited

U.S. PATENT DOCUMENTS

| | | | |
|---|---|---|---|
| 1,256,413 | 2/1918 | Wiswell | 73/864.64 |
| 2,454,952 | 11/1948 | Starkey et al. | 73/864.64 X |
| 2,896,444 | 7/1959 | Forman et al. | 73/864.64 |
| 3,036,638 | 5/1962 | Parsons | 73/864.64 X |
| 3,065,637 | 11/1962 | Landes | 73/864.64 |
| 3,442,017 | 5/1969 | Frerkel | 73/864.64 X |
| 3,596,719 | 8/1971 | Koziski | 175/20 |
| 4,072,059 | 2/1978 | Hamilton | 73/864.04 X |
| 4,252,200 | 2/1981 | Peterson | 175/20 |
| 4,745,802 | 5/1988 | Purfurst | 73/155 |
| 4,950,844 | 8/1990 | Hallmark et al. | 73/864.45 X |

Primary Examiner—Tom Noland
Attorney, Agent, or Firm—Henderson & Sturm

[57] ABSTRACT

A subsurface sampler including a cylindrical casing with portholes to provide access below ground to sample potentially hazardous substances without contaminating investigative probes that are inserted into the interior cavity of the casing. The sampler has an inner sleeve that seals the portholes on the casing during the insertion operation. After the casing is inserted into the ground, the inner sleeve is rotated such that the windows on the sleeve and casing line up exposing the soil to a variety of investigative probes. A tab or wiper is attached to the inner sleeve to clear soil blocking the portholes in the casing and to cut through the "smear" zone immediately along side of the outer surface of the casing. Once the sampler casing is in the ground and portholes are open, a sampling probe is inserted into the interior cavity of the casing following a track or guide system. When soil characterization is complete, the portholes can be closed off by turning the inner sleeve and capping the casing for future analyses, or the interior cavity may be filled with grout. The sampler casing is not intended to be removed unless the area is excavated.

11 Claims, 1 Drawing Sheet

U.S. Patent    May 11, 1993    5,209,129
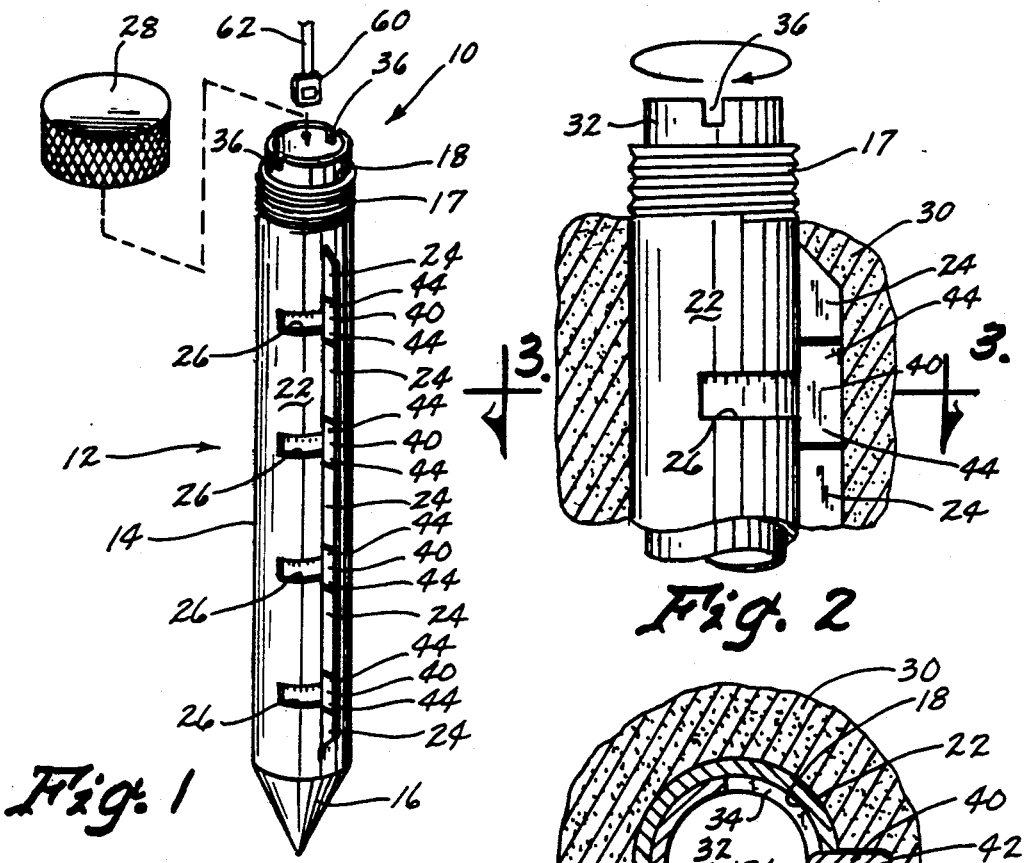
Fig. 1
Fig. 2
Fig. 3
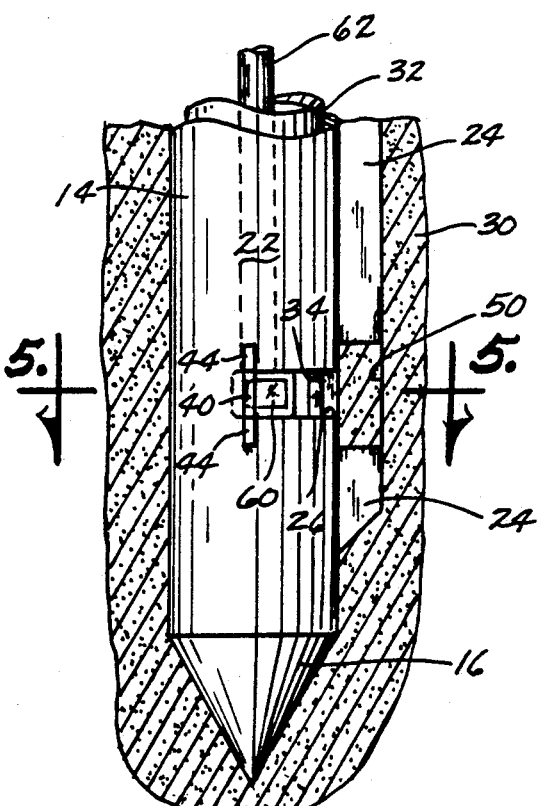
Fig. 4
Fig. 5

SUBSURFACE SAMPLER

TECHNICAL FIELD

This invention relates to subsurface soil samplers and more particularly to a subsurface sampler for highly contaminated soil characterization.

BACKGROUND ART

Various sampling techniques have been used on extremely hazardous waste sites to determine if there are any contaminants in the ground near the surface. Present subsurface sampling techniques involve using the cone penetrometer and standard augering techniques. On uncontrolled hazardous waste sites, both techniques have problems. The cone penetrometer needs to be removed from the ground and cleaned—creating risk to any of the workers involved in the operation and exposing the environment to potentially harmful chemicals. Also, a conduit is created allowing contaminants to move to other levels. Standard augering techniques are inadequate in uncontrolled hazardous waste sites because the contaminated soil is brought to the surface exposing the environment and workers to potentially harmful chemicals.

Those concerned with these and other problems recognize the need for an improved subsurface sampler.

DISCLOSURE OF THE INVENTION

The present invention provides a subsurface sampler including a cylindrical casing with portholes to provide access below ground to sample potentially hazardous substances without contaminating investigative probes that are inserted into the interior cavity of the casing. The sampler has an inner sleeve that seals the portholes on the casing during the insertion operation. After the casing is inserted into the ground, the inner sleeve is rotated such that the windows on the sleeve and casing line up exposing the soil to a variety of investigative probes. A tab or wiper is attached to the inner sleeve to clear soil blocking the portholes in the casing and to cut through the "smear" zone immediately along side of the outer surface of the casing. Once the sampler casing is in the ground and portholes are open, a sampling probe is inserted into the interior cavity of the casing following a track or guide system. When soil characterization is complete, the portholes can be closed off by turning the inner sleeve and capping the casing for future analyses, or the interior cavity may be filled with grout. The sampler casing is not intended to be removed unless the area is excavated.

An object of the present invention is the provision of an improved subsurface sampler.

Another object is to provide a subsurface sampler that is uncomplicated in design and inexpensive.

A further object of the invention is the provision of a subsurface sampler suitable for use on extremely hazardous waste sites.

Still another object is to provide a subsurface sampler suitable for use with a robotic soil sampling system that can provide in situ and real time contaminant analysis.

A still further object of the present invention is the provision of a subsurface sampler that minimizes worker exposure to contaminants.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 1 is an exploded perspective view of the subsurface sampler of the present invention showing the cap removed and the sampling probe positioned to insert into the interior cavity of the casing;

FIG. 2 is an enlarged partial side elevational view showing the casing positioned in the ground with the movable gate in the closed position;

FIG. 3 is a top plan sectional view taken along line 3—3 of FIG. 2;

FIG. 4 is a partial side elevational view showing the movable gate in the open position with the sampling probe positioned in direct communication with a representative material sampling surface; and FIG. 5 is a top plan sectional view taken along line 5—5 of FIG. 4.

BEST MODE FOR CARRYING OUT THE INVENTION

Referring now to the drawings wherein like reference numerals designate identical or corresponding parts throughout the several views, FIG. 1 shows the subsurface sampler (10) of the present invention. The sampler (10) includes a casing (12) having a cylindrical body section (14), a cone-shaped lower end (16), and a threaded top (17). The inner surface 918) of the casing (12) defines an interior cavity (20), and the outer surface (22) carries an outwardly extending fin (24). A number of vertically aligned portholes (26) are formed through the casing (12) extending to one side of the fin (24). A selectively removable cap (28) is received on the threaded top (17) to selectively close the interior top (17) to selectively close the interior cavity (20), and to provide a suitable surface for a vibratory hammer or hydraulic cylinder (not shown) used to drive the casing (12) into the ground (30).

A cylindrical sleeve (32) is matingly received within the casing (12) and includes a number of window openings (34) that may be selectively positioned in registry with the portholes (26). The sleeve (32) acts as a movable gate and may be rotated with respect to the casing (12) by engaging notches (36) with an appropriate tool (not shown), or by any other suitable means. The sleeve (32) is movable between the closed position shown in FIGS. 1-3, and the open position shown in FIGS. 4 and 5.

A wiper mechanism is associated with each of the portholes (26) and includes an outwardly extending tab (40) attached to the sleeve (32) adjacent each window opening (34). Each tab (40) extends outwardly through its associated porthole (26) beyond the smear zone which is immediately adjacent the outer surface (22) of the casing (12). Each tab (40) has an outer end (42) tapered to a point and ears (44) that extend to both sides of the porthole (26) adjacent the outer surface (22) of the casing (12). As the sleeve (32) is rotated from the closed position (FIG. 3), to the open position (FIG. 5), the tab (40) displaces material in the smear zone and exposes a representative material sampling surface (50). A sampling probe (60) is then positioned within the interior cavity (20) by a robotic arm (62) or other suitable means.

In use, the subsurface sampler (10) is driven into the ground (30) with the cap (28) threaded on the top (17) of the casing (12), and the sleeve (32) in the closed position where the tabs (40) are vertically aligned with the protective fin (24). The cap (28) is then removed and the sleeve (32) is rotated to the open position shown in FIGS. 4 and 5. As the sleeve (32) is rotated, the tapered ends (42) of the wipers (40) cut well defined and representative material sampling surfaces (50) outwardly from the smear zone. The sampling probe (60) is then inserted into the interior cavity (20) through the top access opening the selectively positioned at one or more of the portholes (26) in direct communication with the material sampling surface (50). Once sampling is completed, the probe (60) is retracted, the sleeve (32) is rotated to the closed position (FIG. 3), and the cap (28) is replaced. In the event further sampling at a given location is not desired, the interior cavity (20) is filled with grout before replacing the cap (28).

Thus, it can be seen that at least all of the stated objectives have been achieved.

Obviously, many modifications and variations of the present invention are possible in light of the above teachings. It is therefore to be understood that, within the scope of the appended claims, the invention may be practiced otherwise than as specifically described.

We claim:

1. A subsurface sampler, comprising:
   a casing having a top access opening, an inner surface defining an interior cavity, and an outer surface disposed in contact with a material to be sampled;
   a porthole formed through the casing so that the interior cavity may be in direct communication with the material to be sampled;
   movable gate means disposed over the porthole for selectively allowing or preventing direct communication between the interior cavity and the material to be sampled;
   wiper means for displacing material in a smear zone adjacent the outer surface of the casing in the vicinity of the porthole, thereby exposing a representative material sampling surface in direct communication with the interior cavity of the casing through the porthole; and
   a sampling probe received through the top access opening into the interior cavity and selectively positioned at the porthole in direct communication with the material sampling surface.

2. The subsurface sampler of claim 1 wherein the casing includes a cone-shaped lower end to facilitate insertion of the casing into a mass of material to be sampled.

3. The subsurface sampler of claim 1 wherein the casing includes a cylindrical body section.

4. The subsurface sampler of claim 3 wherein the gate means includes a cylindrical sleeve matingly received within the body section of the casing, the sleeve including a window opening and being selectively movable within the casing between a closed position wherein the window opening is disposed adjacent the body section of the casing preventing direct communication between the interior cavity and the material to be sampled, and an open portion wherein the window opening is disposed in registry with the porthole allowing direct communication between the interior cavity and the material to be sampled.

5. The subsurface sampler of claim 4 wherein the sleeve is rotated with respect to the casing to move the sleeve between the closed position and the open position.

6. The subsurface sampler of claim 4 wherein the wiper means includes a tab attached to the sleeve adjacent the window opening, the tab being disposed to extend through the porthole and out from the outer surface of the casing beyond the smear zone, the tab having an outer end movable with respect to material adjacent the outer surface of the casing as the sleeve moves from the closed position to the open position, thereby displacing material in the smear zone and exposing a representative material sampling surface.

7. The subsurface sampler of claim 6 wherein the outer end of the tab is tapered to a point, thereby cutting a well defined sampling surface.

8. The subsurface sampler of claim 6 further including a fin attached to the outer surface of the casing and disposed in alignment with the tab when the sleeve is in the closed position, whereby the tab is shielded by the fin and protected from excessive forces as the casing is inserted into a mass of material to be sampled.

9. The subsurface sampler of claim 6 wherein the tab includes ears that extend laterally out from the porthole adjacent the outer surface of the casing.

10. The subsurface sampler of claim 1 further including a selectively removable cap attached to the casing and disposed to cover the top access opening, whereby the interior cavity may be selectively sealed to minimize human exposure to the material to be sampled.

11. The subsurface sampler of claim 1 wherein a plurality of aligned portholes are formed through the casing.

* * * * *